(12) United States Patent
Zecchino et al.

(10) Patent No.: US 11,890,360 B1
(45) Date of Patent: Feb. 6, 2024

(54) SKIN CARE MASK AND METHOD OF MANUFACTURE

(71) Applicants: Julius Zecchino, New York, NY (US); Marina Turso, Riveredge, NJ (US)

(72) Inventors: Julius Zecchino, New York, NY (US); Marina Turso, Riveredge, NJ (US)

( * ) Notice: Subject to any disclaimer, the term of this patent is extended or adjusted under 35 U.S.C. 154(b) by 0 days.

(21) Appl. No.: 17/951,726

(22) Filed: Sep. 23, 2022

Related U.S. Application Data

(63) Continuation-in-part of application No. 17/881,411, filed on Aug. 4, 2022.

(51) Int. Cl.
| | |
|---|---|
| *A61K 8/02* | (2006.01) |
| *A45D 44/00* | (2006.01) |
| *A61Q 19/10* | (2006.01) |
| *A61Q 19/00* | (2006.01) |

(52) U.S. Cl.
CPC .......... *A61K 8/0212* (2013.01); *A45D 44/002* (2013.01); *A61Q 19/007* (2013.01); *A61Q 19/10* (2013.01); *A61K 2800/28* (2013.01); *A61K 2800/48* (2013.01); *A61K 2800/594* (2013.01); *A61K 2800/805* (2013.01)

(58) Field of Classification Search
None
See application file for complete search history.

(56) References Cited

U.S. PATENT DOCUMENTS

2006/0110416 A1\* 5/2006 Ryles ................... A61K 8/86
424/401
2017/0312301 A1\* 11/2017 Saeki .................. A61Q 19/08

\* cited by examiner

*Primary Examiner* — Nannette Holloman
(74) *Attorney, Agent, or Firm* — Dan De La Rosa

(57) ABSTRACT

A method of manufacturing a clay skin care mask comprising: admixing a lipid blend, polyglutamic acid, pomegranate sterol, barley extract, wheat germ oil, linoleic acid, Montamorillonite, Kaolin Clays, Silver, Zinc Oxide, Glycyrrhetinic Acid, Natural exfoliating beads, and silica beads.

13 Claims, No Drawings

SKIN CARE MASK AND METHOD OF MANUFACTURE

RELATED APPLICATION

This application is a continuation of U.S. application Ser. No. 17/881,411, entitled "MASK" and filed on Aug. 4, 2022.

SUMMARY OF THE INVENTION

The following implementations and aspects thereof are described and illustrated in conjunction with ingredients, formulations and methods that are meant to be exemplary and illustrative, not limiting in scope. The presently claimed invention provides for a unique facial mask that is innovative in the skin care and cosmetic industry. The mask of the present invention combines clays, charcoal and exfoliating particles to deep clean the skin, making it smoother while allowing pores to appear less noticeable. This mask formulation contains hydrating polymers (polyglutamic acid in one embodiment) and a barrier protecting agents (such as pomegranate sterols, linoleic acid, barley and wheat germ extracts). A unique complex of zinc oxide and micro silver BG are used to protect the skin and its microbiome. Micro Silver BG is the only preservative in the formula that wards off unwanted bacteria and fungi, while preserving the microbiome which the skin need to maintain to be healthy. These and other advantages will become apparent to those skilled in the relevant art upon a reading of the following descriptions.

In one embodiment a clay skin care mask that is exfoliating, pore reducing, skin softening, moisture retaining, microbiome protecting formulation comprising a lipid blend, polyglutamic acid, pomegranate sterol, barley extract, wheat germ oil, linoleic acid, Montamorillonite, Kaolin Clays, Silver, Zinc Oxide, Glycyrrhetinic Acid, Natural exfoliating beads, silica beads and mixtures and combinations thereof.

In another embodiment a clay skin care mask formulation comprising at least one lipid blend and at least one moisture binding agent.

In a further embodiment a formulation wherein the lipid blend is selected from group comprising of Linoleic Acid, Linolenic acid, Ceramides, Barley and Wheat germ extracts, Sphingolipids, Sunflower Seed Oil, Grape Seed Oil, and mixtures and combinations thereof.

In yet another embodiment a formulation of wherein the moisture binding agent is selected from group comprising of water, propanediol, hordeumvulgare extract, glycerin, polyglutamic acid, high molecular weight Hyaluronic acid, Sodium hyaluronate, and mixtures and combinations thereof.

In still another embodiment a formulation wherein the formulation is non-irritating, cleansing and moisturizing mask.

In a further embodiment a formulation wherein the peel formulation can be added to cloth, fabric or paper mask.

In another embodiment a formulation further comprising a barrier repair agent, the barrier repair agent is selected from group comprising of linoleic acid, Ceramides, barley, wheat germ, *Amaranthus* Oils, and mixtures and combinations thereof.

In yet a further embodiment a formulation further comprising a barrier protecting agent, said barrier protecting agent is selected from group comprising of pomegranate sterol, cholesterol, lanolin, lanolin sterols, and mixtures and combinations thereof.

In yet another embodiment a formulation further comprising a Microbiome protecting agent, protects against skin pathogens, but helps maintain healthy skin flora, the Microbiome protecting agent is selected from group comprising of Silver, Zinc Oxide, and mixtures and combinations thereof.

In a further embodiment a formulation wherein the lipid blend is from about 0.2% to about 10.0% of said formulation and the moisture binding agent is from about 0.01% to about of the formulation.

In still another embodiment a formulation wherein the barrier repair agent is from about to about 10.0% of the formulation.

In still a further embodiment a formulation wherein the pomegranate sterol is from about to about 5.0% of the formulation.

In yet another embodiment a formulation wherein the barley extract is from about 0.01% to about 5.0% of the formulation.

In yet another embodiment a formulation wherein the wheat germ oil is from about to about 10.0% of the formulation.

In still another embodiment a formulation further comprising additives, preservatives, colorant, and mixtures and combinations thereof from about 0.0% to about 1.0% of the formulation.

In still a further embodiment a formulation having at least one cooling agent, the cooling agent is selected from a group comprising mentha puperita, peppermint, menthol, *leuconostoc*, radish root ferment filtratenn, and mixtures and combinations thereof.

In still yet a further embodiment a formulation of further comprising at least one thickener, the thickener is selected from a group comprising xantham gum, magnesium silicate, *Butyrospermum parkii*, shea butter, *euphorbia* cerifea, candellia and mixtures and combinations thereof.

In still yet another embodiment a formulation further comprising at least one skin benefitting agent, the skin benefitting agent is select from a group comprising caprylyl glycol, *Zingiber officinale*, ginger root, dimethicone, polysilicone-11, squalene, charcoal powder, joba ester and mixtures and combinations thereof.

DETAILED DESCRIPTION OF THE INVENTION

As required, detailed embodiments of the present invention are disclosed herein; however, it is to be understood that the disclosed embodiments are merely exemplary of the invention that may be embodied in various forms. The figures are not necessarily to scale, some features may be exaggerated to show details of particular components. Therefore, specific structural and functional details disclosed herein are not to be interpreted as limiting, but merely as a basis for the claims and as a representative basis for teaching one skilled in the art to variously employ the present invention.

The present invention relates to multiple embodiments including the formulation set forth in Table 1. In one embodiment, the formulation comprises:

| Phase | INCI | % |
| --- | --- | --- |
| A | Water | 41.600 |
| A | Water & Propanediol & Polyglutamic Acid & 1,2-Hexanediol & Caprylyl Glycol | 2.000 |

-continued

| Phase | INCI | % |
|---|---|---|
| A | Water & Honey (White) Extract & Hydroxyacetophenone & 1,2-Hexanediol & Caprylyl Glycol | 2.000 |
| A | Water & Zingiber Officinale (Ginger) Root Extract & Mentha Puperita (Peppermint) Leaf Extract & Leuconostoc/Radish Root Ferment Filtrate | 0.100 |
| A | Menthol | 0.150 |
| B | Xanthan Gum | 0.300 |
| B | Magnesium Aluminum Silicate | 2.500 |
| C | Decyl Glucoside | 5.000 |
| C | Dimethicone & Polysilicone-11 & Butyrospermum Parkii (Shea) Butter | 5.000 |
| C | Punica Granatum (Pomegranate) Sterols | 0.200 |
| C | Squalane & Amaranthus Caudatus Seed Oil & Hordeum Vulgare Extract & Triticum (Wheat) Germ Oil | 0.200 |
| C | Linoleic Acid | 0.200 |
| D | Zinc Oxide (CI 77947) & Triethoxycaprylylsilane | 2.000 |
| E | Glycerin | 5.000 |
| E | Silver | 0.050 |
| F | Glycyrrhetinic Acid | 0.100 |
| F | Kaolin | 25.000 |
| F | Montmorillonite | 3.000 |
| F | Mica & Titanium Dioxide (CI 77891) | 2.000 |
| F | Charcoal Powder | 0.100 |
| G | Stearyl Stearate & Euphorbia Cerifera (Candelilla) Wax & Jojoba Ester | 2.200 |
| G | Hydrated Silica | 1.300 |
|  | Formula Total: | 100.000 |

The first step is to admix Water, Propanediol, Polyglutamic Acid, 1,2-Hexanediol, Caprylyl Glycol to Honey (White) Extract, Hydroxyacetophenone, Caprylyl Glycol Zingiber Officinale (Ginger) Root Extract, Mentha Puperita (Peppermint) Leaf Extract, Leuconostoc, Radish Root Ferment Filtrate, and Menthol to form Phase A. Then admix Xanthan Gum and Magnesium Aluminum Silicate to form phase B. Then heat to and maintain a temperature between 70-55 degrees Celsius. Then admix Decyl Glucoside, Dimethicone, Polysilicone-11, *Butyrospermum Parkii* (Shea) Butter, Punica Granatum (Pomegranate) Sterols, Squalane & *Amaranthus Caudatus* Seed Oil &*Hordeum Vulgare* Extract & *Triticum* (Wheat) Germ, Oil, and Linoleic Acid to from Phase C. Then stop heat and admix Zinc Oxide (CI 77947) & Triethoxycaprylylsilane, Phase A, Phase B, and Phase C to form Phase D. Then admix Glycerin and Silver and add to Phases A through D to form Phase E. Then admix Glycyrrhetinic Acid, Kaolin, Montmorillonite, Mica & Titanium Dioxide (CI 77891), Charcoal Powder to form Phase F. Then admix Stearyl Stearate, *Euphorbia* Cerifera (Candelilla) Wax, Jojoba Ester, and Hydrated Silica to form Phase G. Then Admix Phases A-G mixture well.

Numerous modifications and variations of the present invention are possible in light of the above teachings. It is therefore to be understood that within the scope of the attendant claims attached hereto, this invention may be practiced otherwise than as specifically disclosed herein.

What is claimed is:
1. A method of manufacturing a skin care mask consists of:
admixing water, propanediol, polyglutamic acid, 1,2-hexanediol, caprylyl glycol, honey extract, hydroxyacetophenone, *Zingiber officinale* root extract, mentha puperita leaf extract, *leuconostoc*, radish root ferment filtrate, and menthol to form Phase A;
admixing xanthan gum and magnesium aluminum silicate to form phase B and then heating phase B to maintain a temperature between 70-55 degrees Celsius;
admixing decyl glucoside, dimethicone, polysilicone-11, *Butyrospermum parkii* butter, punica granatum sterols, squalane, *Amaranthus caudatus* seed oil, *Hordeum vulgare* extract, *Triticum* germ, oil, and linoleic acid from Phase C and heat;
after heating, admixing zinc oxide & triethoxycaprylylsilane with Phase A, Phase B, and Phase C to form Phase D;
admixing glycerin and silver to Phase D to form Phase E;
admixing glycyrrhetinic acid, kaolin, montmorillonite, mica, titanium dioxide, charcoal powder to form Phase F;
admixing stearyl stearate, *Euphorbia cerifera* wax, jojoba ester, and hydrated silica to form Phase G; and then admixing Phases E, F and G to form said mask.

2. A method of manufacturing a clay skin care mask consists of: admixing a lipid blend, polyglutamic acid, pomegranate sterol, barley extract, wheat germ oil, linoleic acid, montmorillonite, kaolin clays, silver, zinc oxide, glycyrrhetinic acid, natural exfoliating beads, and silica beads.

3. A method of manufacturing a skin care mask formulation consists of:
admixing at least one lipid blend selected from group consisting of linoleic acid, linolenic acid, ceramides, barley and wheat germ extracts, sphingolipids, sunflower seed oil, grape seed oil, and mixtures and combinations thereof, at least one moisture binding agent selected from group consisting of water, propanediol, *Hordeum vulgare* extract, glycerin, polyglutamic acid, high molecular weight hyaluronic acid, sodium hyaluronate, and mixtures and combinations thereof, at least one barrier repair agent selected from group consisting of linoleic acid, ceramides, barley, wheat germ, *Amaranthus* oils, and mixtures and combinations thereof, at least one barrier protecting agent selected from group consisting of pomegranate sterol, cholesterol, lanolin, lanolin sterols, and mixtures and combinations thereof, at least one microbiome protecting agent selected from group consisting of silver, zinc oxide, and mixtures and combinations thereof, at least one cooling agent selected from a group consisting mentha puperita, menthol, *leuconostoc*, radish root ferment filtrate, and mixtures and combinations thereof, at least one thickener selected from a group consisting of xanthan gum, magnesium silicate, *Butyrospermum parkii* butter, *Euphorbia cerifea*, and mixtures and combinations thereof, and at least one skin benefiting agent selected from a group consisting of caprylyl glycol, *Zingiber officinale*, dimethicone, polysilicone-11, squalene, charcoal powder, jojoba ester and mixtures and combinations thereof, and additives, preservatives, colorant, and mixtures and combinations thereof.

4. The method of claim 3 wherein said formulation is non-irritating, cleansing and moisturizing mask.

5. The method of claim 3 wherein said lipid blend is from about 0.01% to about 10.0% of said formulation and said moisture binding agent is from about 0.01% to about 5.0% of said formulation.

6. The method of claim 3 wherein said barrier repair agent is from about 0.05% to about 10.0% of said formulation.

7. The method of claim 3 wherein said barrier protecting agent is from about 0.10% to about 5.0% of said formulation.

8. The method of claim 3 wherein said barley extract is from about 0.01% to about 5.0% of said formulation.

9. The method of claim 3 wherein said wheat germ extract is from about 0.01% to about 10.0% of said formulation.

10. The method of claim 3 wherein said additives, preservatives, and colorant are from about 0.0% to about 1.0% of said formulation.

11. The method of claim 1 wherein said mask is an exfoliating, pore reducing, skin softening, moisture retaining, and a microbiome protecting formulation.

12. The method of claim 2 wherein said mask is an exfoliating, pore reducing, skin softening, moisture retaining, and a microbiome protecting formulation.

13. The method of claim 3 wherein said mask is an exfoliating, pore reducing, skin softening, moisture retaining, and a microbiome protecting formulation.

\* \* \* \* \*